(12) United States Patent
White

(10) Patent No.: US 11,766,466 B2
(45) Date of Patent: Sep. 26, 2023

(54) EXTRACTION AND PURIFICATION OF CANNABINOIDS

(71) Applicant: M-For, LLC, Oklahoma City, OK (US)

(72) Inventor: Zachary White, Dayton, WA (US)

(73) Assignee: M-For, LLC, Oklahoma City, OK (US)

( * ) Notice: Subject to any disclaimer, the term of this patent is extended or adjusted under 35 U.S.C. 154(b) by 117 days.

(21) Appl. No.: 17/554,850

(22) Filed: Dec. 17, 2021

(65) Prior Publication Data

US 2022/0193164 A1 Jun. 23, 2022

Related U.S. Application Data

(60) Provisional application No. 63/130,012, filed on Dec. 23, 2020.

(51) Int. Cl.
*A61K 36/185* (2006.01)
*A61K 31/05* (2006.01)

(52) U.S. Cl.
CPC ............ *A61K 36/185* (2013.01); *A61K 31/05* (2013.01); *A61K 2236/31* (2013.01); *A61K 2236/333* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 9,376,367 B2 | 6/2016 | Herkenroth et al. |
| 9,474,726 B2 | 10/2016 | Guy et al. |
| 2014/0248379 A1 | 9/2014 | Mueller |
| 2018/0016216 A1 | 1/2018 | Leker et al. |
| 2019/0359550 A1 | 11/2019 | Wohleb et al. |

FOREIGN PATENT DOCUMENTS

| WO | WO2019020738 | 1/2019 |
|---|---|---|
| WO | WO2020121064 | 6/2020 |

OTHER PUBLICATIONS

Written Opinion of the International Searching Authority dated Apr. 15, 2022, PCT/US2021/064171, 4 pages.
International Search Report, PCT/US2021/064171, 4 pages.
Y. Yazaki and T. Aung, Alkaline Extraction of Pinus radiata Bark and Isolation of Aliphatic Dicarboxylic Acids, vol. 42 (1968) No. 6, 4 pages.

*Primary Examiner* — Michael V Meller
(74) *Attorney, Agent, or Firm* — DUNLAP CODDING, PC

(57) ABSTRACT

An improved method for making cannabinoids from plant material utilizes the following steps. Plant material is contacted with an aqueous alkaline solution containing a hydroxide base and essentially no organic solvents, thereby extracting cannabinoids including carboxylic acids and salts and producing an alkaline extract. Non-soluble plant material is removed from the alkaline extract to produce a clarified alkaline extract. The extracted cannabinoids are decarboxylated and the decarboxylated cannabinoids are crystallized/precipitated from the clarified alkaline extract at a pH greater than 7.

13 Claims, 7 Drawing Sheets

EXTRACTION AND PURIFICATION OF CANNABINOIDS

CROSS REFERENCE TO RELATED APPLICATION/INCORPORATION BY REFERENCE STATEMENT

This application claims priority to U.S. Provisional Application 63/130,012 filed Dec. 23, 2020, the entire contents of which are hereby expressly incorporated herein by reference.

BACKGROUND OF THE INVENTIVE CONCEPTS

1. Field of the Inventive Concepts

The present disclosure relates to methods and systems for extraction and purification of cannabinoids and, more particularly, to methods for alkaline extraction and crystallization of cannabinoids.

2. Brief Description of Related Art

The extraction and purification of cannabinoids from the hemp plant *Cannabis sativa* is described in US patent application US 2014/0248379 A1 and references therein. The publication describes the use of a primary solvent to extract cannabinoids, cannabinoid carboxylic acids, terpenes, chlorophyll and other plant derived compounds. While the use of carbon dioxide is the primary extraction method in the patent, the authors outline the use of other acceptable solvents, including, hydrocarbons, aromatic hydrocarbons, chlorinated solvents, and alcohols. The initial extract is further purified through the use of vacuum distillation and chromatography.

Of more specific importance to the cannabidiol (CBD) industry, is US patent application publication 2016/9474726 to GW Pharma Limited. The publication describes the extraction of *Cannabis sativa* L. with carbon dioxide to produce a cannabidiolic acid (CBDA)-rich extract. This extract is heated to induce decarboxylation, winterized, and recrystallized to provide 98%+ CBD as a white solid.

In both cases, "traditional" extraction and post-processing techniques are employed which are generally viewed as laborious due to the number of purification steps involved. US Patent Application US 2016/9376367 B2 improves on this process by producing cannabinoid carboxylic acid salts from solvent extracts of *Cannabis sativa* and recrystallizing the resulting salts to achieve >90 wt. % salt content. The publication further describes the production of neutral cannabinoids from the high purity cannabinoid carboxylic acid salts by heating the isolated salt to 160° C. or at lower temperatures with the application of a metal catalyst. The strategy of using the carboxylic acid functionality greatly reduces the number of purification operations necessary to produce high purity neutral cannabinoids. The author's claim that process applies to $\Delta^9$-tetrahydrocannabinol ($\Delta^9$-THC), cannabidiol (CBD), cannabigerol (CBG), and other naturally occurring trace cannabinoids and homologs thereof. While representing an advancement in terms of purification simplicity, this method still suffers from the necessary use of flammable or high-pressure solvents in the initial step and a liquid-liquid separation process.

From the aforesaid, it follows that a method that takes advantage of the purification potential of the carboxylic acid functionality and avoids the use of dangerous solvents would be of great value.

SUMMARY OF THE INVENTIVE CONCEPTS

The inventive concepts disclosed and claimed herein relate generally to methods and systems for making cannabinoids from cannabinoid carboxylic acid-containing material. In one embodiment, the cannabinoid carboxylic acid-containing material is contacted with an aqueous alkaline solution containing a hydroxide base and essentially no organic solvents. Cannabinoids are extracted into the aqueous solution to produce an alkaline extract, the cannabinoids comprising carboxylic acid salts from the plant material. The non-soluble material is removed from the alkaline extract to produce a clarified alkaline extract. The extracted cannabinoid salts are decarboxylated and the decarboxylated cannabinoids are crystallized or precipitated from the clarified alkaline extract at a pH greater than 7.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
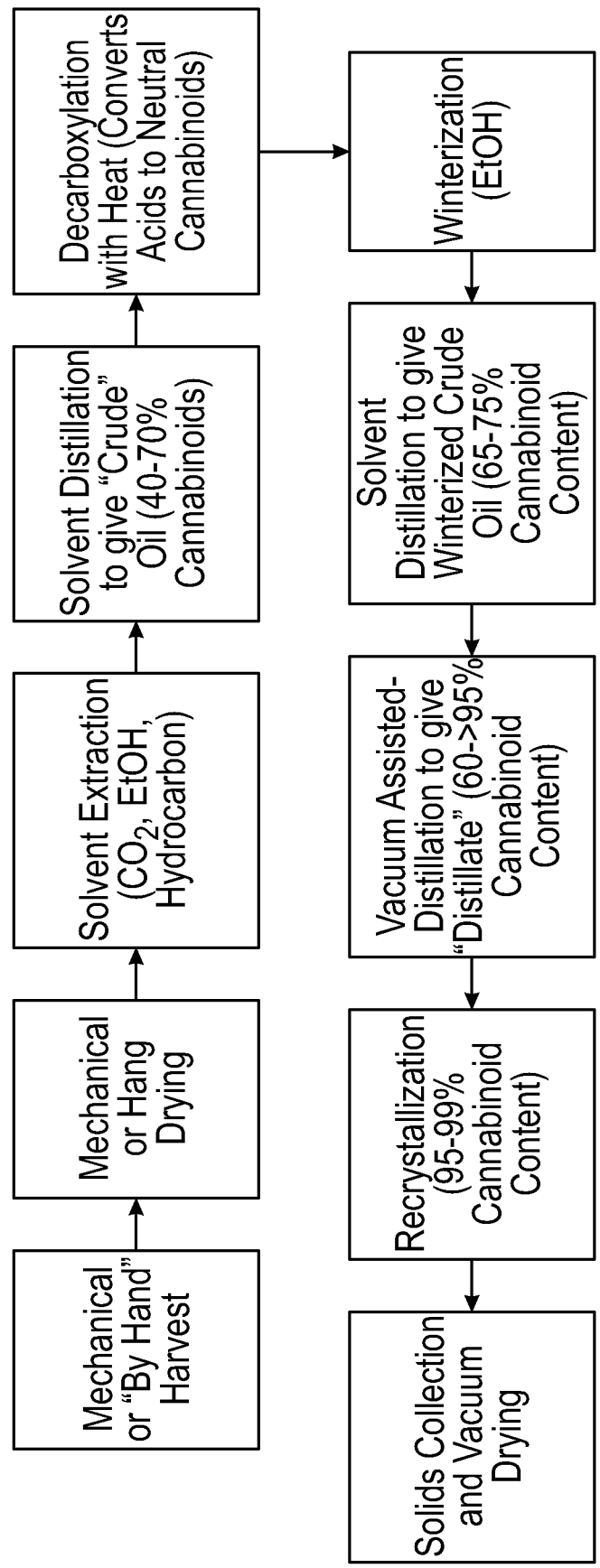
FIG. 1 is a block diagram of traditional processes to purify and concentrate cannabidiol (CBD) from plant material.

Before explaining at least one embodiment of the presently disclosed inventive concept(s) in detail, it is to be understood that the presently disclosed inventive concept(s) is not limited in its application to the details of construction and the arrangement of the components or steps or methodologies set forth in the following description or illustrated in the drawings. The presently disclosed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed inventive concept(s) shall have the meanings that are commonly understood by those of ordinary skill in the art. Further, unless otherwise required by context, singular terms shall include pluralities and plural terms shall include the singular.

All of the articles and/or methods disclosed herein can be made and executed without undue experimentation in light of the present disclosure. While the articles and methods of the presently disclosed inventive concept(s) have been described in terms of preferred embodiments, it will be apparent to those skilled in the art that variations may be applied to the articles and/or methods and in the steps or in the sequence of steps of the method described herein without departing from the concept, spirit, and scope of the presently disclosed inventive concept(s). All such similar substitutes and modifications apparent to those skilled in the art are deemed to be within the spirit, scope, and concept of the presently disclosed inventive concept(s).

As utilized in accordance with the present disclosure, the following terms, unless otherwise indicated, shall be understood to have the following meanings:

The use of the word "a" or "an" when used in conjunction with the term "comprising" in the claims and/or the specification may mean "one", but it is also consistent with the meaning of "one or more," "at least one," and "one or more than one." The use of the term "or" in the claims is used to mean "and/or" unless explicitly indicated to refer to alternatives only or that the alternatives are mutually exclusive, although the disclosure supports a definition that refers to only alternatives and "and/or."

Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "associate" as used herein will be understood to refer to the direct or indirect connection of two or more items.

The presently disclosed inventive process provides a low-cost alternative for extracting carboxylic acids and converting them to their neutral cannabinoid derivatives. The process avoids the safety concerns associated with flammable solvents and reduces the number of necessary purification steps. Additionally, there is a reduction in pre-processing steps associated with drying of the *Cannabis sativa* material before traditional solvent extraction. Further, the process is amenable to achieving an "Organic" certification.

Conventional processing of *cannabis* is summarized in FIG. 1, wherein plants are harvested mechanically or by hand, and then dried mechanically or by hanging and air drying. While FIG. 1 shows conventional processing generally, there is a large range of process variables and wt. % at the different processing steps. For example, cryogenic temperatures during the solvent extraction process can eliminate the need for winterization (removal of plant waxes, fats, lipids, and the like) thus avoiding lipid extraction altogether and yielding a high wt. % cannabinoid content for the crude oil. Additionally, distillate qualities are affected by the distillation method, wt. % of the input crude material, and the number of distillation passes performed. Further, crystallization purity is largely determined by the number of times recrystallization is performed. It is near impossible to achieve 99%+ CBD content without at least two recrystallization runs.

Figure 2:
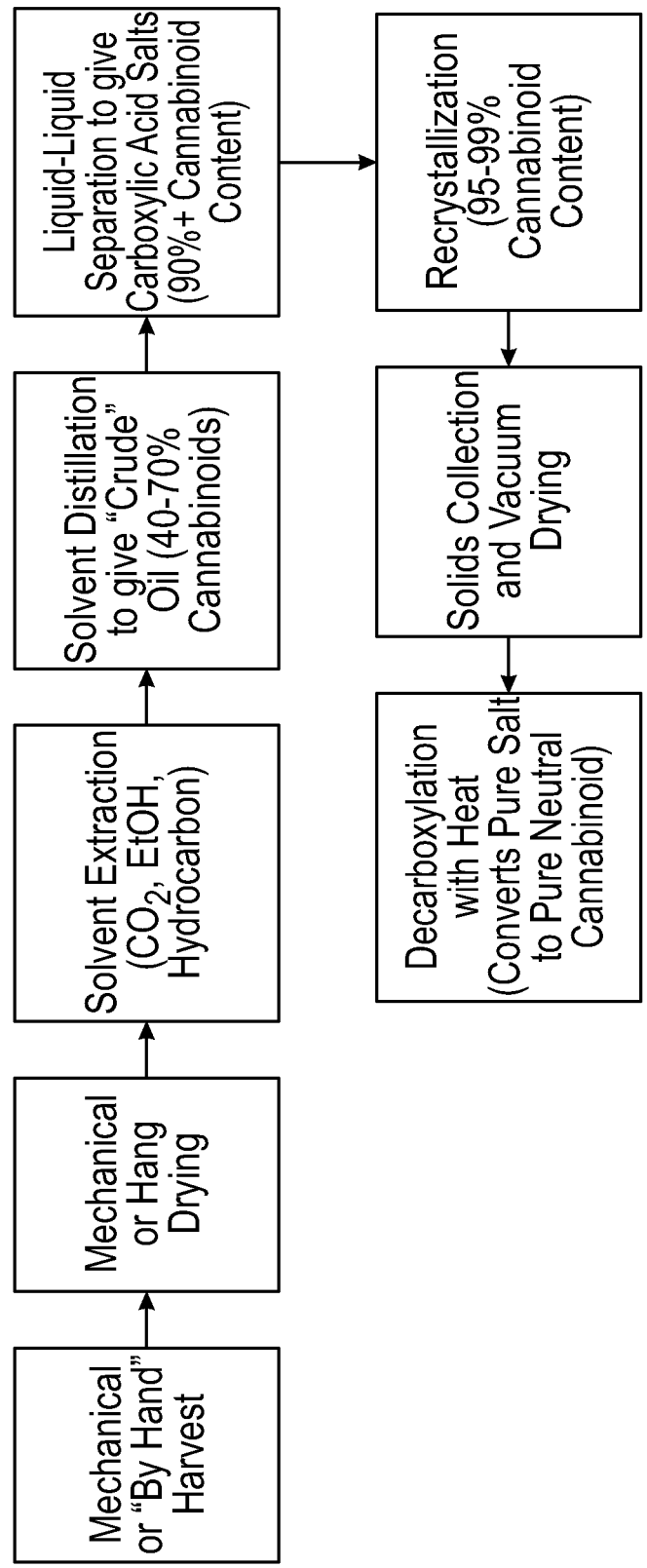
FIG. 2 is a block diagram of a prior art process to purify and concentrate CBD from plant material according to US 2016/9376367.

The presently described inventive process does not use organic solvents for the initial extraction as required by most prior art processes such as, for example, US 2016/9376367 summarized in FIG. 2. The prior art process shown in FIG. 2 uses organic solvents for the initial extraction to form a "crude" oil. Carboxylic acid salts are the formed through a liquid-liquid extraction of the crude oil or extract and followed by recrystallization. While this prior art scheme does convert the cannabinoid carboxylic acid salts to neutral cannabinoids, this is done after recrystallization of the carboxylic acid salts and not directly from the extract liquid as is the case in the present invention. Furthermore, these prior art processes must either heat to 160° C. or use a catalyst to induce decarboxylation of the cannabinoid carboxylic acid salt. In contrast, in the presently described inventive methods, decarboxylation occurs directly from the extract liquid rapidly at 60° C. in less than 3 hours and even occurs at room temperature in about 5 days without using a catalyst.

Figure 3:
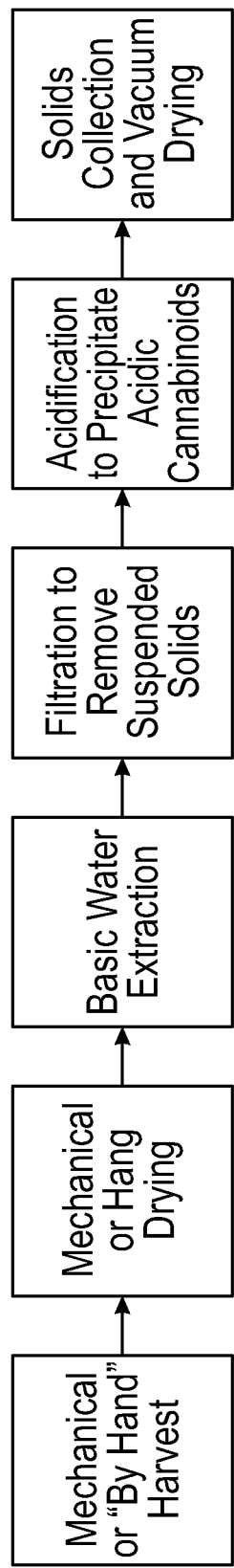
FIG. 3 is a block diagram of a prior art process to purify and concentrate CBD from plant material according to US 2019/0359550.

An improved prior art method for making acidic cannabinoids from plant material is described in US 2019/0359550 and summarized in FIG. 3. Plant material is contacted with an aqueous alkaline solution containing a hydroxide base and no organic solvents, thereby extracting cannabinoids including carboxylic acid salts to produce an alkaline extract. Non-soluble plant material is removed from the alkaline extract to produce a clarified alkaline extract. The extracted cannabinoid acids are precipitated by the addition of a strong acid and collected as a microcrystalline powder. Obtaining the neutral cannabinoids from this process requires decarboxylation and recrystallization.

Figure 4:
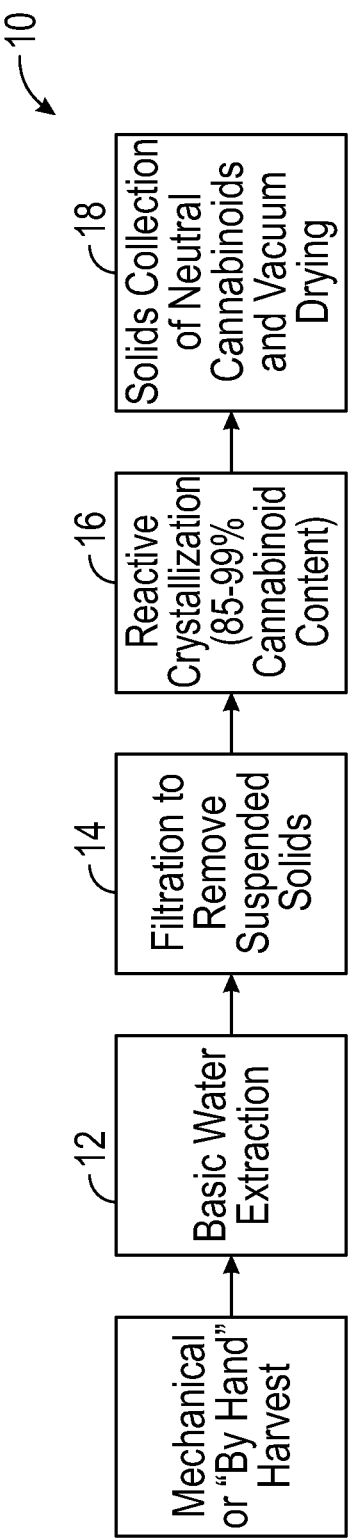
FIG. 4 is a block diagram of an embodiment of the presently disclosed inventive process to purify and concentrate CBD from plant material.

Turning now to FIG. 4, a novel method 10 for making cannabinoids from cannabinoid carboxylic acid-containing material is shown. In one embodiment, the cannabinoid carboxylic acid-containing material is plant material such as hemp that has been harvested mechanically or by hand. The cannabinoid carboxylic acid-containing material is contacted in a basic water extraction step 12 with an aqueous alkaline solution containing a hydroxide base and essentially no organic solvents. Cannabinoids are extracted into the aqueous solution to produce an alkaline extract, the cannabinoids comprising carboxylic acid salts from the cannabinoid carboxylic acid-containing material. The non-soluble material is removed from the alkaline extract by, for example, filtration as in step 14 to produce a clarified alkaline extract. In step 16 the extracted cannabinoid acid salts are decarboxylated and the decarboxylated cannabinoids are crystallized or precipitated from the clarified alkaline extract at a pH greater than 7. This crystallization/precipitation step 16 is sometimes referred to herein as "reactive crystallization" and, as explained in detail hereinafter, the reactive crystallization is used for the direct isolation of neutral cannabinoids from basic extracts of cannabinoid carboxylic acid salts. The crystals or precipitate are then collected and dried in step 18.

Typically, the cannabinoid carboxylic acid-containing material comprises plant material such as a hemp variety or any mechanically processed form of hemp. In one embodiment, the plant material comprises hash, kief, dry sift, and the like. Hash and kief refer to the collection or concentration of loose *cannabis* trichomes, which can be accumulated by, for example, sifting the *cannabis* flowers or buds with a mesh screen or sieve. Like some other *cannabis* concentrates, it contains a much higher concentration of cannabinoid acid and cannabinoids than that of the *cannabis* flower from which it is derived.

Cannabinoid acids can react with strong inorganic bases to form salts with increased water solubility. Suitable hydroxide bases include, but are not limited to, NaOH, KOH, $NH_4OH$, and combinations thereof. In one embodiment, the hydroxide base comprises NaOH.

The concentration of hydroxide base can vary widely, but should be sufficient to achieve a pH greater than pH 7 to insure solubilization of the cannabinoid from the plant. In one embodiment, the aqueous alkaline solution contains sufficient NaOH to provide a pH greater than about 8 in the clarified alkaline extract. For example, the pH of the clarified alkaline extract can be 9 or greater, or even at a pH range of about 12 to about 13.5.

Generally, higher alkalinities increase the solubility of the cannabinoid acids and increase extraction efficiency from the plant material. In one embodiment, the plant extraction and subsequent decarboxylation and crystallization occur in 1 N NaOH.

The extraction process can be performed in a stirred tank, an extraction centrifuge, or other equipment known to those skilled in the art.

The aqueous alkaline solution contains no organic solvent as do many traditional processes. Further, because the process is water-based, traditional mechanical or hang drying of the plants can minimized or avoided completely.

Non-soluble plant material can be removed from the alkaline extract using filtration. In one embodiment, a majority of the undissolved plant material is removed and washed using a centrifuge. Centrate can then be clarified in, for example, a polishing filter. Centrifugation, filtering and polishing steps and equipment are well understood by those skilled in the art. In one embodiment, a secondary wash is used after the initial extraction and wash.

Figure 5:
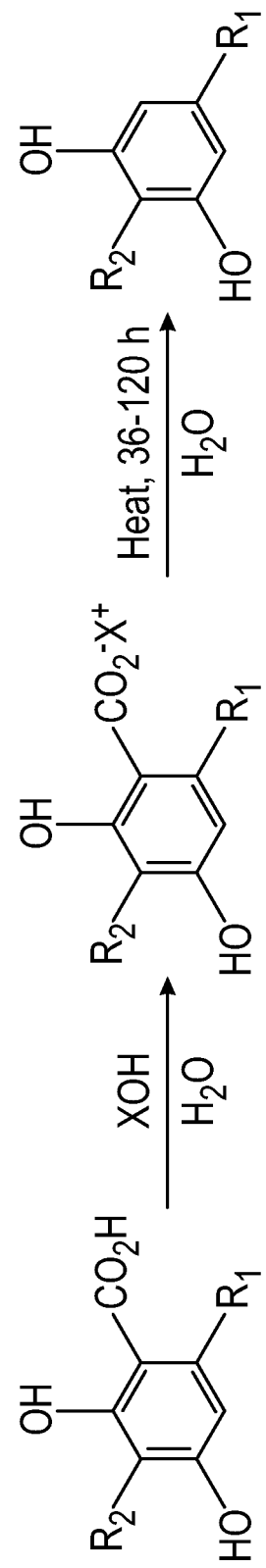
FIG. 5 is a general reaction scheme for decarboxylating and crystallizing/precipitating cannabinoids.

Cannabinoid acid salts are soluble but not stable in alkaline solutions. Decarboxylation of the dissolved cannabinoid acid salts, and subsequent crystallization/precipitation of the decarboxylated cannabinoid, occurs with increasing time and temperature as shown in FIG. 5. Thus, the time, temperature and agitation during this process step can be optimized for increased efficiency, purity, and decreased cost. It should also be noted that this natural tendency to decarboxylate and crystallize/precipitate from alkaline aqueous solutions is why it is sometimes desirable to cool the extraction solution below ambient temperatures to ensure that decarboxylation and crystallization/precipitation does not occur during the extraction step and cause cannabinoids to be lost with the insoluble plant material waste.

When heating the polished extract, an oil-in-water emulsion can form. The oil contaminates the cannabinoid product and causes operational difficulties. It was discovered that the oil is actually an oxidation product and can be avoided by sparging the alkaline solutions and extracts with an inert gas to remove oxygen and avoid oxidation. Examples of suitable inert gases include, but are not limited to, $N_2$, He, Ar, and combinations thereof. In one embodiment, nitrogen is used to sparge the alkaline solution prior to contacting with the plant material and after. It can also be used to move the solutions to avoid adding air with pumps.

In one embodiment, the cannabinoid carboxylic acid-containing material or hemp is extracted with alkaline solution prepared with fresh (tap) water, and the decarboxylated cannabinoid crystals/precipitates are washed with fresh water and then dried. In another embodiment, the fresh water is further purified by reverse osmosis (RO). Reverse osmosis operation and equipment is well understood by those skilled in the art. Using an RO water extraction and wash increases the purity of the product substantially as shown in Table 1 below. Chemical analyses of product decarboxylated cannabinoid crystals/precipitate after a tap water extraction and wash are compared to Example 5 product analyses after an RO water extraction and wash.

TABLE 1

Effect of RO Water Extraction and Wash versus Tap Water on Product Purity

| | Limit of Quantitation | Tap Water | RO Water |
| --- | --- | --- | --- |
| CBC, % | 0.0284 | ND | ND |
| CBCA, % | 0.0543 | | ND |

TABLE 1-continued

Effect of RO Water Extraction and Wash versus Tap Water on Product Purity

| | Limit of Quantitation | Tap Water | RO Water |
|---|---|---|---|
| CBCV, % | 0.018 | | ND |
| CBD, % | 0.0242 | 96.87 | 99.8 |
| CBDA, % | 0.013 | ND | ND |
| CBDV, % | 0.0182 | ND | 0.145 |
| CBDVA, % | 0.0063 | | ND |
| CBG | 0.0172 | ND | ND |
| CBGA | 0.0147 | ND | ND |
| CBN | 0.0335 | | ND |
| CBNA | 0.0181 | | ND |
| CBL, % | 0.0335 | | ND |
| CBLA, % | 0.0371 | | ND |
| CBN, % | 0.0169 | | ND |
| CBNA, % | 0.0181 | | ND |
| Total Δ9-THC, % | | ND | ND |
| Total CBD, % | | 96.87 | 99.8 |
| CBE, % | 0.0284 | | ND |
| CBT, % | 0.0543 | | ND |
| As, ppb | 20 | | ND |
| Cd, ppb | 20 | | ND |
| Pb, ppb | 20 | | ND |
| Hg, ppb | 50 | | ND |
| Pesticides, ppb | 100 | | ND |

The RO-extracted and washed product above was additionally tested for microbials, mycotoxins, and residual solvents. In each category there were none detected.

Filtrate from the decarboxylated cannabinoid filtration and wash step is also referred to herein as barren aqueous solution since the cannabinoid content has been substantially removed. The barren aqueous solution can be filtered through an alkaline tolerant nanofiltration membrane to recover hydroxide base. The recovered hydroxide base can then be recycled to the plant extraction step. In one embodiment, a 200 mwco (molecular weight cut-off) nanofiltration membrane is used to recover the base and reject non-desirable botanical extracts such as lignin, hemicellulose, pectin and the like. In another embodiment, hydroxide base is recovered for recycle from the clarified alkaline extract prior to crystallizing/precipitating decarboxylated cannabinoids.

Figure 6:
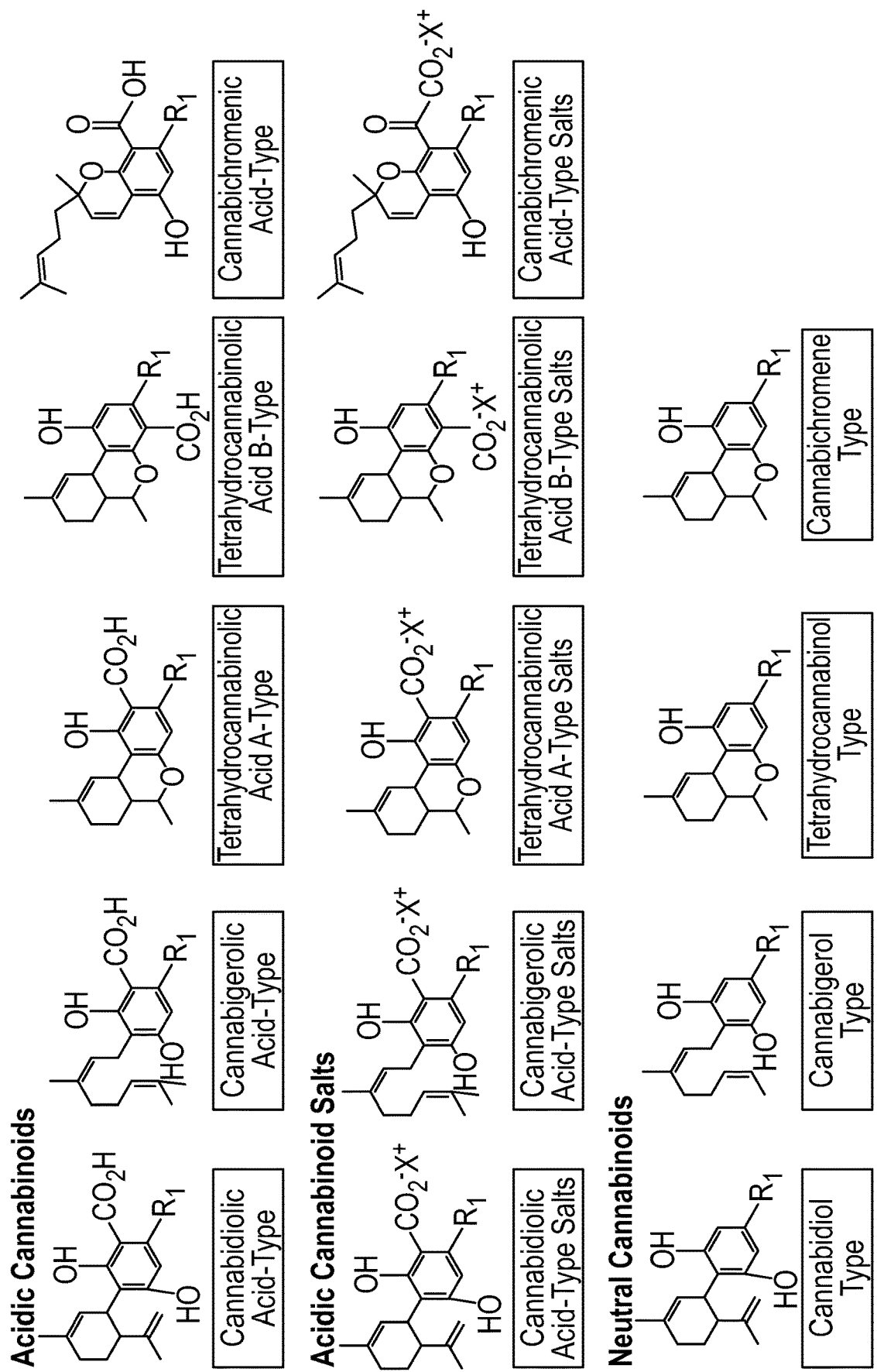
FIG. 6 shows example cannabinoids for which the presently disclosed process is applicable.

The inventive process can be used to process any crystalline/precipitated, neutral cannabinoid that has a cannabinoid carboxylic acid precursor (whether extracted from *Cannabis sativa* or of synthetic preparation). Of particular importance is the processing of plant material to include CBG and cannabigerolic acid (CBGA) which is the most abundant cannabinoid varietal for hemp crops in 2020 other than CBD/CBDA varietals. FIG. 6 shows nonlimiting examples of cannabinoids recoverable using the presently disclosed process.

Thus, the presently disclosed inventive process provides for the direct extraction of cannabinoid carboxylic acids and their subsequent salts from *Cannabis sativa* plant materials or cell cultures utilizing a base (organic or inorganic, preferably sodium hydroxide) in a suitable solvent (tap water) and inducing a reactive crystallization/precipitation process in the resulting aqueous extract to precipitate/crystallize neutral cannabinoids (>85 wt. %) directly from the aqueous extract. The duration of the process and purity (>85 to >98 wt. %) of the product obtained from the crystallization/precipitation process can be controlled with temperature and by the rate and manner of agitation. Additionally, "wet" *Cannabis sativa* plants can be used because the traditional need for drying before extraction is removed when extracting with an aqueous medium. The inventive process also benefits from the ability to use caustic-compatible nanofiltration membrane technology to recover the high pH process water and reuse any unconsumed sodium hydroxide (or other base used).

The present approach was not considered possible by the cannabinoid industry due to two commonly held beliefs. First, it was believed that the extraction of plant cell wall components such as lignin, hemicellulose, pectin, etc. from *Cannabis sativa* in basic media presents a burdensome purification hurdle once an acid is added to precipitate the cannabinoid carboxylic acids. Secondly, it was believed that basic extracts of *Cannabis sativa* are prone to oxidation resulting in the hypothesized irreversible formation of HU-331 (R. Mechoulam et al., J. Med. Chem., 2004, 47, 3800), a purple oxidation product derived from CBD. It was surprisingly discovered that crystallization/precipitation of cannabinoids can actually occur without addition of an acid while leaving other plant derived components still solubilized in the basic water. It was further discovered that the extract solution can be thoroughly degassed with nitrogen via an in-line sparging stone to prevents any appreciable oxidation before the crystallization/precipitation. In one embodiment, up to 5% sodium sulfite can be added as an antioxidant before the crystallization/precipitation.

Hence the invention provides a low-cost alternative for extracting carboxylic acids and converting them to their neutral cannabinoid derivatives while avoiding the safety concerns associated with flammable solvents and reducing the number of necessary purification steps. A further advantage consists of reducing the need for pre-processing steps associated with drying of the *Cannabis sativa* material before traditional solvent extraction. A yet further advantage consists of establishing a procedure amenable to achieving an "Organic" certification in addition to the improvements in cost, processing steps, and safety.

In the following examples, specific compositions and test conditions are described. However, the present inventive concept(s) is not be limited in its application to the specific experimentation, pilot plant procedures, and result. Rather, the Examples are simply provided as one of various embodiments and are meant to be exemplary, not exhaustive.

COMPARATIVE EXAMPLES

Figure 7:
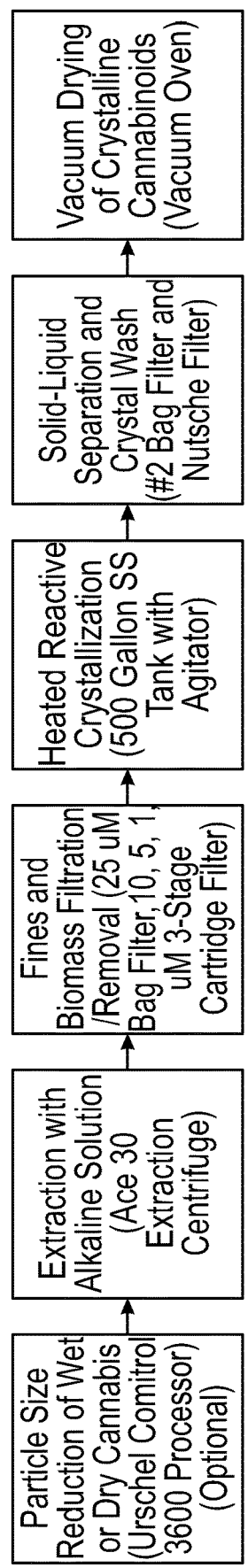
FIG. 7 is a block diagram of the pilot plant operated in examples 4, 5, and 6.
Figure 8:
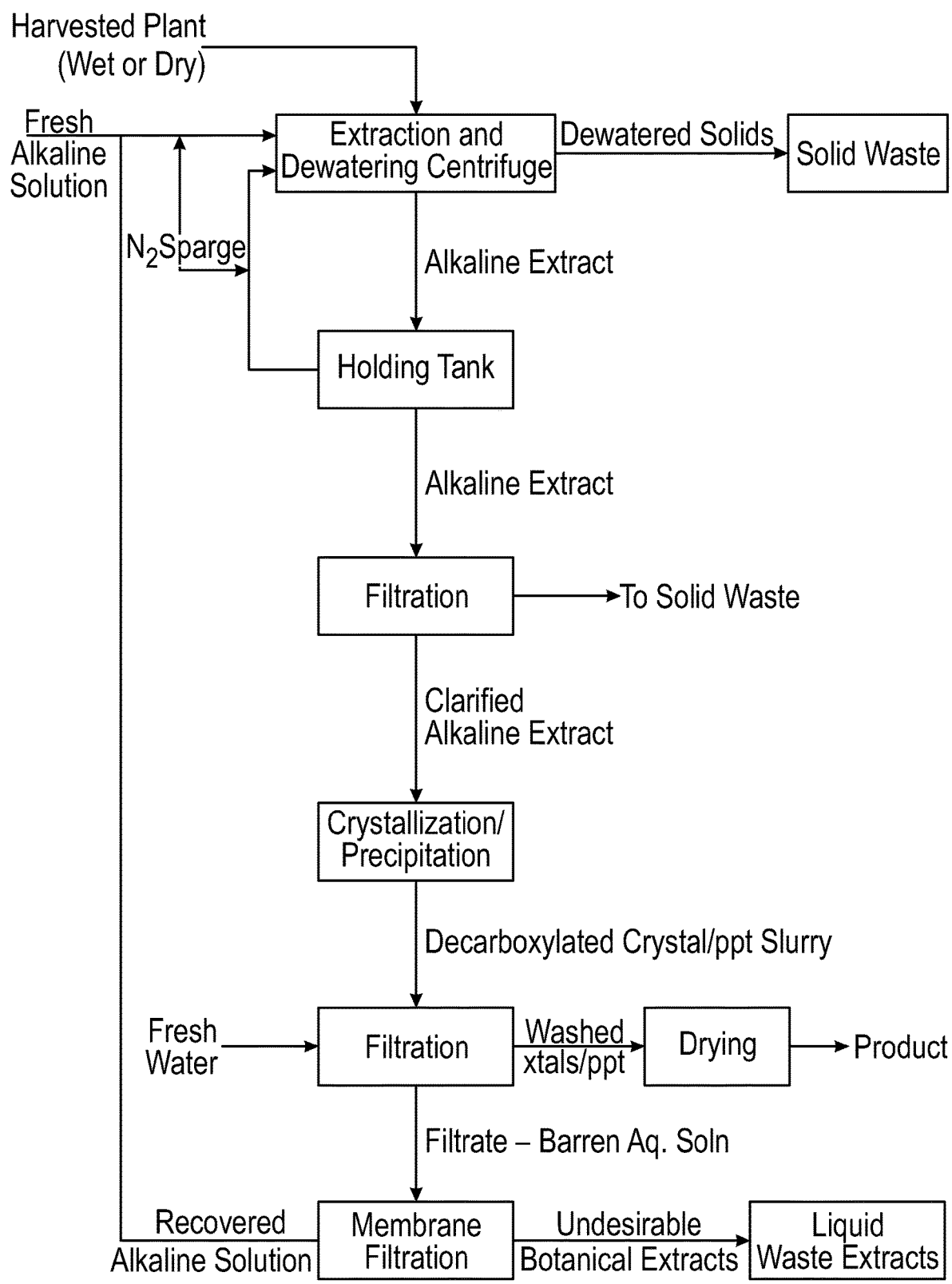
FIG. 8 is a block flow diagram of the pilot plant operated in the examples.

FIG. 7 and FIG. 8 summarize a pilot scale process for testing the presently disclosed process.

Example 1 (With Inert Gas Purging)

In one test, 55.25 kg of flowering tops and leaves of industrial hemp (of the CBDawg Hemp variety, but any variety is possible) were packed into six 100-micron centrifuge bags and subsequently extracted with 50 gallons of 1 N NaOH solution in water at room temperature. Each bag was extracted for 10 min inside a 50-gallon centrifuge (Ace 30 Spinner) and then the liquid was pumped through a 25-micron bag filter to a 100-gallon stainless steel storage tank. The extraction liquid was degassed with nitrogen at the pump outlet using a 4-inch sparge stone. The extracted hemp was dewatered using the centrifuge (ramp up to 1800 rpm), and the extracted material was removed. The next bag was placed in the centrifuge and the process was repeated for all six bags. After all the hemp material had been extracted, the bulk extract was filtered through a series of three cartridge filters (10-micron, 5-micron, 1-micron) to a second 100-gallon stainless steel holding tank (using 5 psi of nitrogen to transfer the liquid).

A portion of this liquid (40 L, 10.57 gallons) was transferred to a 50 L dual jacketed glass reactor. The reactor jacket was heated to 43° C., and the solution was vigorously agitated for 40 h. After 40 h, all the sodium salt of cannabidiolic acid ($Na^+CBDA^-$) had been decarboxylated (based off HPLC-UV-VIS analysis of extract), the agitation was stopped, and the formed solids settled to the bottom of the reactor. 30 L of the extract liquid was removed by dip tube and fresh reverse osmosis (RO) water was added to wash the solids for 30 min. This process was repeated 2 more times. The solids were then collected using medium porosity qualitative filter paper (Sterlitech) in a 6-inch pressure vessel, and the cake was further washed with RO water. The resulting tan solid was dried for 48 h in a vacuum oven after which 300 g of a tan powder were recovered, the tan powder having a purity of >98 wt. % CBD as determined by HPLC-UV-VIS. A 45% yield was calculated based on available CBDA concentration in the starting hemp material.

Example 2 (Without Inert Gas Purging)

33.2 kg of flowering tops and leaves of industrial hemp (of the Cherry Wine variety, but any variety is possible) were packed into five 100-micron centrifuge bags and subsequently extracted with 30 gallons of 1 N NaOH solution in water at room temperature. Each bag was extracted for 10 min inside a 50-gallon centrifuge (Ace 30 Spinner) and then the liquid was pumped through a 25-micron bag filter to a 100-gallon stainless steel storage tank. The extraction liquid was not degassed at any time. The extracted hemp was dewatered using the centrifuge (ramp up to 1800 rpm), and the extracted material was removed. The next bag was placed in the centrifuge and the process was repeated for all six bags. After all the hemp material had been extracted, the bulk extract was filtered through a series of three cartridge filters (10-micron, 5-micron, 1-micron) to a second 100-gallon stainless steel holding tank (using 5 psi of nitrogen to transfer the liquid).

A portion of this liquid (40 L, 10.57 gallons) was transferred to a 50 L dual jacketed glass reactor. The reactor jacket was heated to 43° C., and the solution was vigorously agitated for 40 h. After 40 h, all the sodium salt of cannabidiolic acid ($Na^+CBDA^-$) had been decarboxylated (based off HPLC-UV-VIS analysis of extract), the agitation was stopped, and the formed solids settled to the bottom of the reactor. 30 L of the extract liquid was removed by dip tube and fresh RO water was added to wash the solids for 30 min. This process was repeated 2 more times. The solids were then collected using medium porosity qualitative filter paper (Sterlitech) on a Buchner funnel and the cake was further washed with RO water. The resulting tan solid was dried for 48 h in a vacuum oven after which 120 g of a tan powder were recovered, the tan powder having a purity of >96 wt. % CBD as determined by HPLC-UV-VIS. A 21% yield was calculated based on available CBDA concentration in the starting hemp material.

Example 3

50.1 kg of dried flowering tops and leaves of industrial hemp (of the Oregon CBD's White CBG variety, but any variety is possible) were packed into 100-micron centrifuge bags and subsequently extracted. Each centrifuge bag was extracted at room temperature as follows: 50 gallons of a NaOH solution (5 kg NaOH in 100 gallons of water) from Tank 1 was filtered through a 25-micron bag and into the centrifuge containing the bag of hemp. Each bag was extracted for 10 min before the liquid was pumped back to Tank 1. The extraction liquid was degassed with nitrogen at the pump outlet using a 4-inch sparge stone. A second wash was performed in the same manner using 50 gallons from Tank 2. The extracted hemp was dewatered using the centrifuge (ramp up to 1800 rpm), and the extracted material was removed. The next bag was placed in the centrifuge and the process was repeated until all hemp had been processed.

After all the hemp material had been extracted, the bulk extract (100 gallons total) was filtered through a series of three cartridge filters (10-micron, 5-micron, 1-micron) to a 100 gallon agitated tank. The tank was heated with an immersion heater to 45° C., and the solution was gently agitated for 40 h. After 40 h, all the sodium salt of cannabigerolic acid ($Na^+CBGA^-$) had been decarboxylated (based off HPLC-UV-VIS analysis of extract), the solution was cooled to 1° C. (jacket temperature) over 24 hr, and the formed solids were collected in a 5-micron #2 bag filter. The resulting solids were washed with RO water on a 6-inch Buchner Funnel until no more coloration was observed in the filtrate. The solids were then dried at 43° C. in a vacuum oven for 48 hr after which 3.4 kg of a off-white powder were recovered, the off-white powder having a purity of >98 wt. % CBG as determined by HPLC-UV-VIS. A 64% yield was calculated based on available CBGA concentration in the starting hemp material.

Example 4

224 kg of dried flowering tops and leaves of industrial hemp (of the CBDawg Hemp variety, but any variety is possible) were packed into 100-micron centrifuge bags and subsequently extracted. Each centrifuge bag was extracted at room temperature as follows: 50 gallons (out of 250 gallons) of a NaOH solution (12.5 kg NaOH in 250 gallons of water) from Tank 1 was filtered through a 25-micron bag and into the centrifuge containing the bag of hemp. Each bag was extracted for 10 min before the liquid was pumped back to Tank 1. The extraction liquid was degassed with nitrogen at the pump outlet using a 4-inch sparge stone. A second wash was performed in the same manner using 50 gallons (out of 250 gallons) from Tank 2. The extracted hemp was dewatered using the centrifuge (ramp up to 1800 rpm), and the extracted material was removed. The next bag was placed in the centrifuge and the process was repeated until all hemp had been processed.

After all the hemp material had been extracted, the bulk extract (500 gallons total) was filtered through a series of three cartridge filters (10-micron, 5-micron, 1-micron) to a 530 gallon agitated tank. The tank was heated with an immersion heater to 50° C., and the solution was gently agitated for 40 h. After 40 h, all the sodium salt of cannabidiolic acid ($Na^+CBDA^-$) had been decarboxylated (based off HPLC-UV-VIS analysis of extract), the solution was cooled to 12° C. (solution temperature) over 24 hr, and the formed solids were collected in a 5-micron #2 bag filter. The collected solids were transferred to a 50 L Nutsche filter and further washed with RO (pH~5.5) was until no more color was observed in the filtrate and the pH of the filtrate was below 6. The resulting tan solid was dried under vacuum for 48 hr inside the Nutsche filter (jacket temperature of 70° C.) after which 3.98 kg of a tan powder were recovered, the tan powder having a purity of >95 wt. % CBD as determined by HPLC-UV-VIS. A 40% yield was calculated based on available CBDA concentration in the starting hemp material.

Example 5

227 kg of dried flowering tops and leaves of industrial hemp (of the CBDawg Hemp variety, but any variety is possible) were packed into 100-micron centrifuge bags and subsequently extracted. All water used in this experiment was purified through an RO system before used. Each centrifuge bag was extracted at room temperature as follows: 50 gallons (out of 250 gallons) of a NaOH solution (12.5 kg NaOH in 250 gallons of water) from Tank 1 was filtered through a 25-micron bag and into the centrifuge containing the bag of hemp. Each bag was extracted for 10 min before the liquid was pumped back to Tank 1. The extraction liquid was degassed with nitrogen at the pump outlet using a 4-inch sparge stone. A second wash was performed in the same manner using 50 gallons (out of 250 gallons) from Tank 2. The extracted hemp was dewatered using the centrifuge (ramp up to 1800 rpm), and the extracted material was removed. The next bag was placed in the centrifuge and the process was repeated until all hemp had been processed.

After all the hemp material had been extracted, the bulk extract (500 gallons total) was filtered through a series of three cartridge filters (10-micron, 5-micron, 1-micron) to a 530 gallon agitated tank. The tank was heated with an immersion heater to 50° C., and the solution was gently agitated for 40 h. After 40 h, all the sodium salt of cannabidiolic acid ($Na^+CBDA^-$) had been decarboxylated (based off HPLC-UV-VIS analysis of extract), the solution was cooled to 12° C. (solution temperature) over 24 hr, and the formed solids were collected in a 5-micron #2 bag filter. The collected solids were transferred to a 50 L Nutsche filter and further washed with RO (pH~5.5) until no more color was observed in the filtrate and the pH of the filtrate was below 6. The resulting tan solid was dried under vacuum for 48 hr inside the Nutsche filter (jacket temperature of 70° C.) after which 4.93 kg of a tan powder were recovered, the tan powder having a purity of >99.5 wt. % CBD (>0.1% CBDV) as determined by HPLC-UV-VIS. A 54% yield was calculated based on available CBDA concentration in the starting hemp material.

Example 6

320 kg of "wet" flowering tops and leaves of industrial hemp (of the mixed variety, but any variety is possible) were packed into 100-micron centrifuge bags and subsequently extracted. "Wet" is defined as being over 70% water by weight and is obtained by harvesting the plant directly from the field without any subsequent drying. In this case, the material was frozen and stored until extraction. Each centrifuge bag was extracted at room temperature as follows: 50 gallons (out of 250 gallons) of a NaOH solution (9.5 kg NaOH in 250 gallons of water) from Tank 1 was filtered through a 25-micron bag and into the centrifuge containing the bag of hemp. Each bag was extracted for 10 min before the liquid was pumped back to Tank 1. The extraction liquid was degassed with nitrogen at the pump outlet using a 4-inch sparge stone. A second wash was performed in the same manner using 50 gallons (out of 250 gallons) from Tank 2. The extracted hemp was dewatered using the centrifuge (ramp up to 1800 rpm), and the extracted material was removed. The next bag was placed in the centrifuge and the process was repeated until all hemp had been processed.

After all the hemp material had been extracted, the bulk extract (500 gallons total) was filtered through a series of three cartridge filters (10-micron, 5-micron, 1-micron) to a 530 gallon agitated tank. The tank was heated with an immersion heater to 50° C., and the solution was gently agitated for 40 h. After 40 h, all the sodium salt of cannabidiolic acid ($Na^+CBDA^-$) had been decarboxylated (based off HPLC-UV-VIS analysis of extract), the solution was cooled to 12° C. (solution temperature) over 24 hr, and the formed solids were collected in a 5-micron #2 bag filter. The collected solids were transferred to a 50 L Nutsche filter and further washed with RO (pH~5.5) was until no more color was observed in the filtrate and the pH of the filtrate was below 6. The resulting tan solid was dried under vacuum for 48 hr inside the Nutsche filter (jacket temperature of 70° C.) after which 1.14 kg of a tan powder were recovered, the tan powder having a purity of >95 wt. % CBD as determined by HPLC-UV-VIS. A 20% yield was calculated based on available CBDA concentration in the starting hemp material.

Although the presently disclosed inventive concept(s) has been described in conjunction with the specific language set forth herein above, it is evident that many alternatives, modifications, and variations will be apparent to those skilled in the art. Accordingly, it is intended to embrace all such alternatives, modifications, and variations that fall within the spirit and broad scope of the presently disclosed inventive concept(s). Changes may be made in the construction and the operation of the various components, elements, and assemblies described herein, as well as in the steps or the sequence of steps of the methods described herein, without departing from the spirit and scope of the presently disclosed inventive concept(s).

What is claimed is:

1. A method for purifying cannabidiol from *cannabis*, the method comprising:
   a. contacting *cannabis* with an aqueous alkaline solution of a strong inorganic base selected from the group consisting of NaOH, KOH, $NH_4OH$, and combinations thereof, to extract cannabidiolic acid from the *cannabis* and produce an aqueous alkaline extract of *cannabis*, wherein no organic solvents are used;
   b. purging the aqueous alkaline extract of *cannabis* with an inert gas selected from the group consisting of nitrogen, argon, helium, and combinations thereof to produce a purged aqueous alkaline extract of *cannabis*;
   c. removing non-soluble material from the purged aqueous alkaline extract of *cannabis* via filtration, centrifugation or both to produce a clarified extract of *cannabis*;
   d. decarboxylating the clarified extract of *cannabis* at a temperature sufficient to convert the cannabidiolic acid to cannabidiol;
   e. crystallizing and precipitating the cannabidiol from the clarified extract at a pH greater than 7 to produce crystallized and precipitated cannabidiol;
   f. filtering the crystallized and precipitated cannabidiol to produce 85% to 100% cannabidiol and a barren aqueous solution of the strong inorganic base; and
   g. recycling and reusing the barren aqueous solution of the strong inorganic base from step (f) and then extracting new *cannabis* with the barren aqueous solution of a strong inorganic base selected from the group consisting of NaOH, KOH, $NH_4OH$, and combinations thereof.

2. The method of claim 1, wherein the *cannabis* is not dried prior to step (a).

3. The method of claim 1, wherein the *cannabis* is hemp.

4. The method of claim 1, wherein the strong inorganic base is NaOH.

5. The method of claim 1, wherein the step (c) of removing non-soluble material from the purged aqueous alkaline extract of *cannabis* to produce a clarified extract of *cannabis* is performed using centrifugation.

6. The method of claim 1, wherein the crystallizing and precipitating of the cannabidiol from the clarified extract is performed at a pH greater than 9 to produce the crystallized and precipitated cannabidiol.

7. The method of claim 1, wherein the inert gas is nitrogen.

8. The method of claim 1, wherein the clarified extract of *cannabis* is heated to a temperature in a range of from about 35° C. to about 75° C. to increase the rate of decarboxylation in step (d).

9. The method of claim 1, wherein the step (d) of decarboxylating and step (e) of crystallizing and precipitating occur at a pH range of about 12 to about 13.5.

10. The method of claim 1, wherein no acid is added to the clarified extract of *cannabis*.

11. The method of claim 1, wherein the barren aqueous solution of the strong inorganic base is filtered using an alkaline tolerant nanofiltration membrane prior to step (g).

12. The method of claim 1, further comprising washing the 85% to 100% cannabidiol from step (f) with water purified by reverse osmosis.

13. The method of claim 1, wherein the aqueous alkaline solution of a strong inorganic base is initially prepared using water purified by reverse osmosis.

\* \* \* \* \*